United States Patent [19]

Shimamura et al.

[11] 4,063,817
[45] Dec. 20, 1977

[54] CHEMICAL REACTION VELOCITY MEASURING APPARATUS

[75] Inventors: Teruo Shimamura, Yokosuka; Yoshio Fukami, Yokohama; Hidetoshi Mori, Kawasaki, all of Japan

[73] Assignee: Nippon Kogaku K.K., Tokyo, Japan

[21] Appl. No.: 641,267

[22] Filed: Dec. 16, 1975

[30] Foreign Application Priority Data

Dec. 26, 1974   Japan .............................. 50-148386

[51] Int. Cl.² .......................... G01J 3/42; G01J 3/46; G01N 21/22
[52] U.S. Cl. ........................................ 356/93; 356/97; 356/180; 356/195; 356/201; 356/205; 23/230 R; 23/253 R
[58] Field of Search ...................... 356/88, 93, 95, 96, 356/180, 184, 188, 195, 201, 205, 206, 97; 23/230 R, 230 B, 253 R

[56] References Cited

U.S. PATENT DOCUMENTS

| 3,523,737 | 8/1970 | Wood et al. | 356/180 |
| 3,748,044 | 7/1973 | Liston | 356/180 |
| 3,790,279 | 2/1974 | Skala | 356/205 |
| 3,811,780 | 5/1974 | Liston | 356/180 |
| 3,847,486 | 11/1974 | McCabe | 356/96 |
| 3,901,600 | 8/1975 | Johnson, Jr. et al. | 356/88 |
| 3,915,644 | 10/1975 | Walraven | 23/253 R |
| 3,963,909 | 6/1976 | Atwood et al. | 23/230 R |

Primary Examiner—Vincent P. McGraw
Attorney, Agent, or Firm—Fitzpatrick, Cella, Harper & Scinto

[57] ABSTRACT

An apparatus for measuring velocity of chemical reaction by detecting change in light absorbance which stands in proportional relation with time, which comprises arranging plural samples at regular spacings, advancing said samples intermittently at constant intervals, detecting the absorbances with two colorimetric detecting means crossing said samples and measuring the difference between the absorbences thereby determining the reaction velocity of said samples.

17 Claims, 21 Drawing Figures

CHEMICAL REACTION VELOCITY MEASURING APPARATUS

BACKGROUND OF THE INVENTION

1. Field of the Invention

The present invention relates to a reaction velocity measuring apparatus for rapid and accurate measurement of the velocity of chemical reactions.

2. Description of the Prior Art

The principle of the measurement of velocity of chemical reaction is explained in the following with particular reference, as an example, to an enzymatic reaction.

It is already known to determine the amount of enzyme indirectly from the reaction velocity per unit time or enzyme activity by measuring the reaction velocity of a reaction catalyzed by said enzyme. Under certain conditions, i.e. under suitable temperature conditions with a suitably low enzyme concentration and a suitably high substrate concentration, each molecule of enzyme independently reacts with the substrate with a velocity proportional to the concentration of enzyme. In case the reaction velocity is proportional to the amount of enzyme and does not depend on time, the enzymatic reaction proceeds at a constant velocity. Stated differently the amount of reaction product stands in a linear relationship with time, signifying that the light absorption coefficient becomes proportional to time.

The measurement of the reaction velocity of enzyme is usually achieved by measuring the difference of light absorbance in 1 minute while such proportional relationship stands, and the IU, i.e. the amount of enzyme per 1 liter is defined by the following equation:

$$IU = \Delta A \cdot K$$

wherein $\Delta A$ represents the difference of light absorbance in 1 minute, and K is a constant (hereinafter referred to as K factor).

In the prior art the velocity of an enzymatic reaction is measured by recording the light absorbance of coenzyme on a recorder, reading the difference of light absorbance in 1 minute within a range where such linear relationship is visually observable and multiplying said difference by said K factor manually or by measuring light absorbance at suitable time intervals, electrically substracting and converting thus obtained value to obtain the difference in 1 minute, and multiplying said difference by said K factor.

In case of determining the enzyme activity from the change of light absorbance in the course of a reaction, the period required for such determination is represented by (number of samples) × (time of measurement necessary for one sample). On the other hand the colorimetry method wherein the reaction velocity is calculated from the light absorbance in the chemical equilibrium state after the completion of chemical reaction requires a period represented by (time necessary for reaction) ÷ (number of sample) × (period of measurement necessary for one sample) since is this case plural samples are simultaneously subjected to reaction and then to measurements after the completion of reaction. The former requires a shorter time and is therefore advantageous if the number of samples is limited, but takes several times longer period in comparison with the latter which requires only several seconds for the measurement of each sample, if a considerably large number of samples is to be measured. With respect to the accuracy of measurement, however, the latter is inferior since the measurement is realized in a range where the light absorbance is not linearly correlated with the reaction velocity. For this reason the former method is more adequate for a more accurate measurement of the enzyme activity. With further respect to the former method, the usually employed way with electric subtraction is realized by the measurement of light absorbance A at time $t_1$ followed by that of light absorbance A' at time $t_2$ to determine a ratio $(A' - A)/(t_2 - t_1)$.

In this manner the measuring apparatus is not in operation between two measurements at $t_1$ and $t_2$, and has therefore considerable idle time. It has therefore been proposed to utilize such idle time between $t_1$ and $t_2$ for the measurements of other samples thereby improving the efficiency of apparatus and increasing the number of treated samples. In this case the sample measured at time $t_1$ has to be returned to the original position at $t_2$ since a sample has to be subjected to two measurements. For this purpose there have been proposed devices in which plural samples are arranged in a reciprocating rack or arranged in circular positions. However such devices are inadvantageous as the number of samples accomodated is inevitably limited. More specifically the devices of this kind become inevitably large in dimensions, if the number of samples is increased, and require complicated electric circuitry as the memory circuits explained later are required in same number as the samples. Thus, there have to be frequent interruptions of operations for the replacement of measured samples with unmeasured ones.

SUMMARY OF THE INVENTION

The present invention is applicable to the method of determining the enzyme activity by means of the change of light absorption in the course of chemical reaction, and the first object thereof is to provide an apparatus for measuring the velocity of chemical reaction capable, without the above-mentioned drawbacks, of utilizing the above-mentioned idle time between $t_1$ and $t_2$ for the measurements of other samples thereby improving the efficiency of apparatus and increasing the number of treated samples.

The second object of the present invention is to provide an apparatus for measuring the velocity of chemical reaction which, in addition to the achievement of the aforementioned first object, is freed from the undesirable effect on the measured values resulting from eventual drifts in the electrical systems such as light source, detector, amplifier etc. in the time period from $t_1$ to $t_2$ in order to effect the measurements at $t_1$ and $t_2$ under as same conditions as possible and to ensure an as high accuracy as possible.

Figure 11:
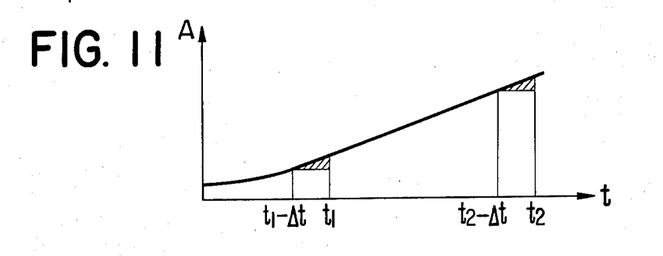
FIG. 11 is a drawing showing the relation between absorbance of sample and time.

Further, in case of an enzymatic reaction it is to be noted that the reaction is initiated by a non-linear so-called lag phase, and takes certain time lag before it reaches the linear portion (as shown in FIG. 11 indicating light absorption A in ordinate against time in abscissa) where the measurements are to be effected for accurate determination of enzyme activity.

The third object of the present invention, therefore, is to provide an apparatus for measuring the velocity of chemical reaction which is added, to the apparatus achieving the afore-mentioned first and second objects, with a linearity monitor capable of judging whether the measurements are effected in such linear portion and indicating the result of such judgment.

The present invention will be further clarified by the following description with specific reference to the embodiments thereof shown in the attached drawings, wherein the like parts and elements are designated by like numerals and symbols throughout therein.

DESCRIPTION OF THE PREFERRED EMBODIMENTS

Figure 3A:
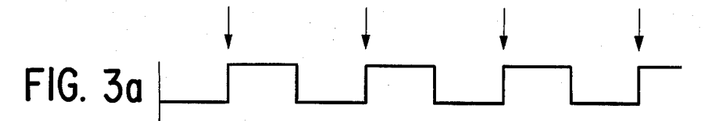
FIGS. 3a – 3c a pulse chart for explaining the function of principal portion of the first embodiment.
Figure 3B:
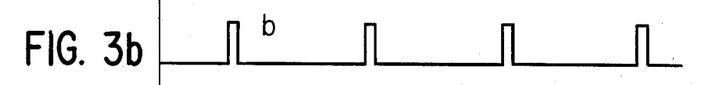
Figure 3C:
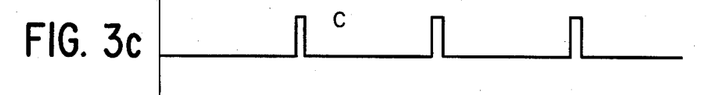

In the following explained is a first embodiment of the present invention achieving the aforementioned first object thereof with reference to FIGS. 1 - 3.

Figures 1, 2:
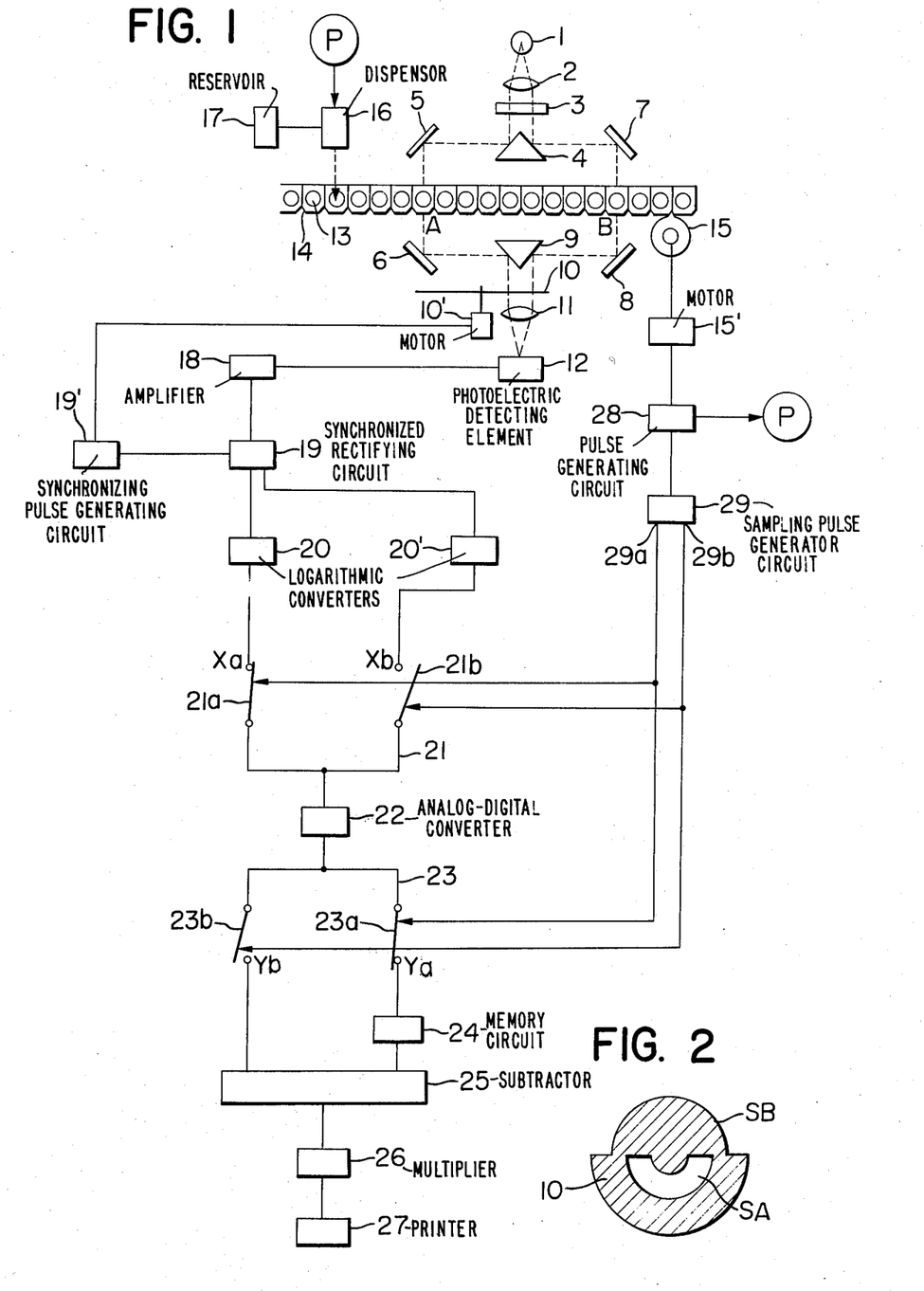
FIG. 1 is a drawing showing a first embodiment of the present invention.
FIG. 2 is a drawing showing the chopper employed in the first embodiment.

Referring to FIG. 1, the numeral 1 indicates a light source, 2 is a convex lens for converting the light from the light source into a parallel beam, 3 is an interference filter for selecting a light of a particular wavelength, 4 is a rectangular prism for splitting said light beam into two directions, 5, 6, 7, and 8 are plane mirrors for converting the direction of thus split beams A and B, 9 is a rectangular prism for directing the beams A and B into one direction, and 10 is a chopper of a shape shown in FIG. 2 for alternately passing the beams A and B.

As shown in FIG. 2, the chopper is provided with a semi-circuit slit SA for passing said beam A, and with a semi-circular recess SB for passing said beam B in a position opposite to the slit SA. 10' is a motor for rotating the chopper 10. Further, 11 is a convex lens for focusing the light beams from the rectangular prism 9, 12 is a photoelectric detecting element provided on the focusing position of said beams, 13 are reaction cuvettes in which the samples are reacted, 14 is sample holders for holding the reaction cuvettes, 15 is a cam driven by a motor 15' for intermittent advancement of the sample holder 14 in the arrow direction, 17 is a reservoir for chemical reagent, and 16 is a dispenser for supplying said chemical reagent to the reaction cuvette 13 in response to the pulse signals from a synchronizing pulse generating circuit 28 which also supplies synchronized pulse signals to the cam 15 for advancing the sample holders.

The sample holders 14 are mutually connected. Further the reaction cuvettes 13 are so arranged as to stop in the positions allowing the light beams A and B to pass therethrough when the sample holders 14 are intermittently advanced by means of the cam 15, and the revolution of the motor 15' is so selected that a reaction cuvette reaches the position of beam B one minute after passing the position of beam A. The photoelectric detector 12 receives the beams A and B alternately and converts the beams into electric signals which are amplified by an amplifier 18. 19 is a synchronized rectifying circuit which functions is synchronization with the signals of the beams A and B and which is synchronized with the pulse signals from a synchronizing pulse generating circuit 19' which are synchronized with the functions of the chopper 10. 20 and 20' are logarithmic converters for converting the signals from the synchronized rectifying circuit 19 into absorption coefficient signals, the converters 20 and 20' respectively receiving the signals of beams A and B. Further, 28 is a synchronizing pulse generating circuit synchronized with the motor 15' to generate pulses which are initiated upon completion of the advancements of the sample holder 14 by the cam 15, as shown in FIG. 3a. Also 29 is a sampling pulse generating circuit which releases pulses as shown in FIG. 3b from the terminal 29a thereof in synchronization with the start of output pulses from the pulse generating circuit 28 and pulses as shown in FIG. 3c from the terminal 29b thereof in synchronization with the end of the output pulses from the pulse generating circuit 28.

21 is a switch provided with contacts $X_a$ and $X_b$, and switching arms 21a and 21b. 22 is an analog-digital converter, and 23 is a switch provided with contacts $Y_a$ and $Y_b$, and switching arms 23a and 23b. The switches 21 and 23 are controlled by the sampling pulse generating circuit 29 in such a way that the switching arms 21a and 23a come into contact respectively with the contacts $X_a$ and $Y_a$ only upon receipt of the pulses b shown in FIG. 3b from the terminal 29a and that the switching arms 21b and 23b come into contact respectively with the contacts $X_b$ and $Y_b$ only upon receipt of the pulses c from the terminal 29b. 24 is a memory circuit composed of ten-unit shift register, for successively memorizing the output signals from the contact $Y_a$ of switch 23. The first signal is at first memorized in the first memory element and then is transferred to the second memory element upon receipt of the second signal which is then memorized in the first memory element. In this manner, upon receipt of the tenth signal, the first signal is transferred to the tenth memory element and the tenth signal is memorized in the first memory element. 25 is a subtractor which is supplied with the signal memorized in the tenth memory element of the memory circuit 24 as the minuend, and also supplied with the output signal from the contact $Y_b$ of switch 23 as the subtrahend. In this manner the subtractor 25 provides an output representing the difference of light absorbance in one minute. 26 is a multiplier for miltiplying the output of the subtractor with the K factor to obtain the amount of enzyme in international units. 27 is a printer for the printout of the output of the multiplier 26.

With the structure as explained above, the sample holders 14 are intermittently advanced in the arrow direction by means of the rotation of cam 15. The reaction cuvettes 13 contain the chemical reagent supplied from the reservoir 17 through the dispenser 16, and the light transmission of the samples is measured by the light beams A and B and with the photoelectric detector 12. The output signals of the detector 12 are converted into light absorbance signals separately for the beam A and for the beam B through 18 - 20', and the absorbance signals of the beam A and beam B are respectively supplied to the contacts $X_a$ and $X_b$ alternately and in synchronization with the motor 10'. In this manner the signal of beam A is memorized in the memory circuit 24 when the switch 21 is closed at the contact $X_a$, and then the signal of beam B is supplied to the subtractor 25 when the switch 21 is switched to the contact $X_b$. This operation is repeated each advancement of the sample holders 14. After a sample has passed the light beam A, the minuend input of the subtractor 25 remains zero until said sample reaches the light beam B, and upon arrival thereof (after one minute) the subtractor 25 provides the difference of absorbance of said sample in one minute. In this manner the subtractor provides the difference of absorbance upon each advancement of the samples, and the amount of enzyme in each sample is printed by the printer 27.

Figure 4:
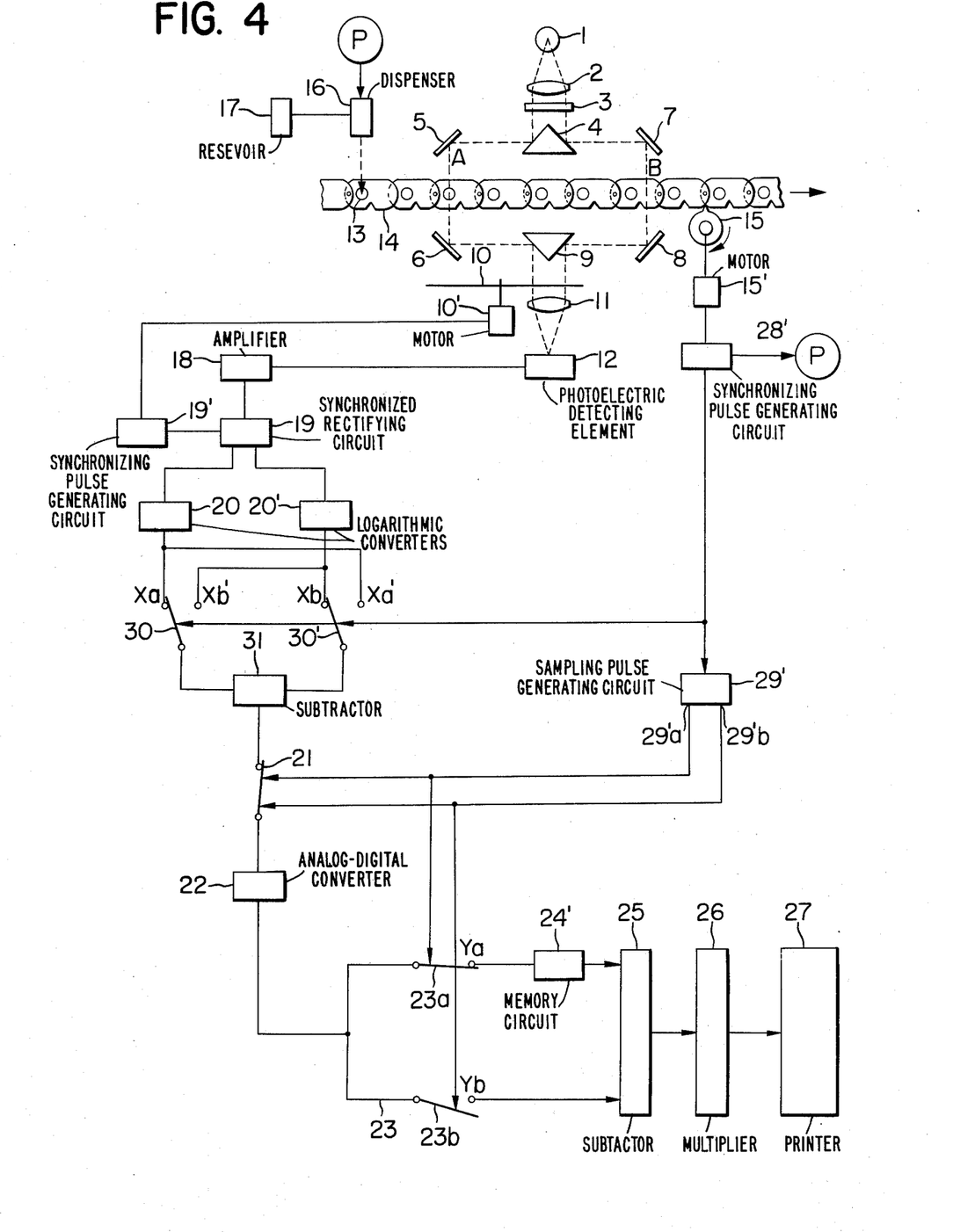
FIG. 4 is a drawing showing a second embodiment of the present invention.
Figure 5A:
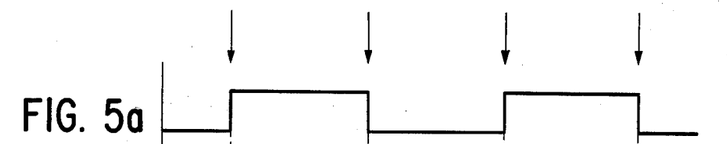
FIGS. 5a – 5c are a pulse chart for explaining the function of principal portion of the second embodiment.
Figure 5B:
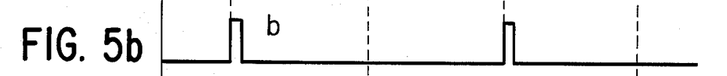
Figure 5C:
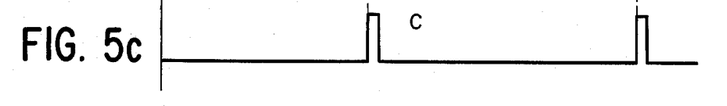
Figure 6:
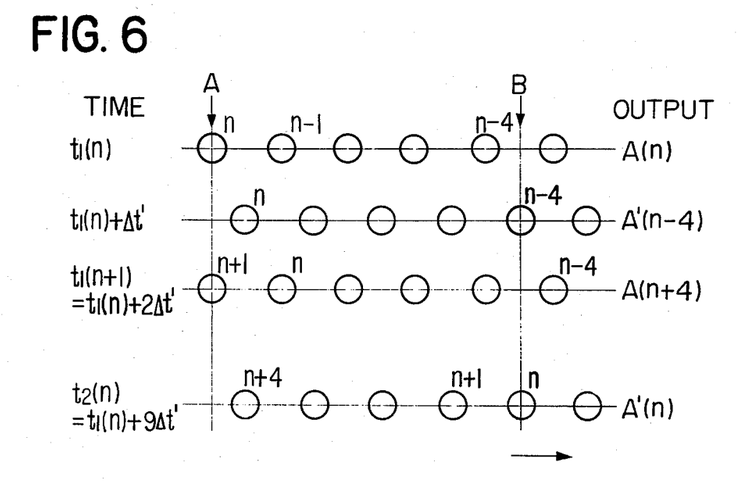
FIG. 6 is a drawing for explaining the function of the second embodiment.

In the following there is explained a second embodiment for achieving the second object of the present invention, with particular reference to FIGS. 4 - 6. Referring to FIG. 4, 13 and 14 are reaction cuvettes and sample holders respectively, each of the sample holder being dimensioned to accomodate two reaction cuvettes but containing only one reaction cuvette to leave a vacant space therein. The vacant space in the present embodiment corresponds to the volume of one reaction cuvette, but it can be made smaller if desirable. In such case each advancement should also be made smaller than in the present embodiment according to the actual spacing of the reaction cuvettes. In comparison with the first embodiment, therefore, every other cuvette is eliminated in the present embodiment. The cam 15 advances the sample holders by a distance corresponding to one reaction cuvette, or by a distance corresponding to one half of sample holder, at each advancement, as will be further explained in connection with FIG. 4. Referring to FIG. 4, the light beam A is in a sample position and located at the $n$-th sample at a time $t_1(n)$, and the light beam B is in a reference side position. In this state the absorbance of the $n$-th sample at time $t_1(n)$ is measured. Then at the time $t_1(n) + \Delta t'$ the sample holders are advanced by a distance corresponding to one reaction cuvette to position where the beam A is at a reference side and the beam B at a sample side. At this state the absorbance $A'(n - 4)$ of the $(n - 4)$-th sample is measured. At the time $t_2(n) = t_1(n) + 9 \Delta t'$ after repeated advancements at each time interval of $\Delta t$, the light beam A is positioned at a reference side and the light beam B is position at the $n$-th sample to allow the measurement of absorbance $A'(n)$ of the $n$-th sample at time $t_2(n)$ thereby allowing to determine the difference from the abosrbance $A(n)$ as to be explained later. 30 and 30' are switches with electrical switching elements which are connected to the terminals $X_a$ and $X_b$ or terminals $X_a'$ and $X_b'$ respectively when the beam A is in a sample side and beam B is in a reference side or when the beam A is in a reference side and beam B is in a sample side. This switching is controlled by a synchronizing pulse generating circuit 28' which changes the state thereof at the completion of each advancement of samples, in synchronization with aforementioned motor 15', to generate pulse signals as shown in FIG. 5a. More specifically the switches 30 and 30' are contacting the terminals $X_a$, $X_b$ or terminals $X_a'$, $X_b'$ respectively when said pulse generating circuit releases high or low level signal. 31 is a subtractor which receives the output signal of switch 30 as the minuend and the output signal of switch 30' as the subtrahend. The output of the subtractor 31 is supplied to a switch 21. 29' is a sampling pulse generating circuit which generates pulse signals $b$ as shown in FIG. 5b from the terminal 29'a thereof at the initiation of the output signal as shown in FIG. 5a from the synchronizing pulse generating circuit 28' and pulse signals $c$ as shown in FIG. 5c from the terminal 29'b thereof at the termination of said output signal.

21 is a switch which is closed only upon receipt of the pulse $b$ from the terminal 29'a or of the pulse $c$ from the terminal 29'b.

23 is a switch provided with a contact $Y_a$ connected to a memory circuit 24, a contact $Y_b$ connected to the input of a subtractor 25, and switching arms 23a and 23b, of which 23a comes into contact with the terminal $Y_a$ upon receipt of the pulse $b$ from the terminal 29'a and 23b comes into contact with the terminal $Y_b$ upon receipt of the pulse $c$ from the terminal 29'b. The memory circuit 24 is composed of a five-unit shift register. The remaining part of this embodiment is identical to that in the foregoing embodiment.

In the present embodiment, the sample holders 14 are intermittently advanced in the arrow direction by the rotation of cam 15. When the light beams A and B are respectively positioned in a sample side and a reference side, the photoelectric detector 12 receives the signals therefrom alternately and the initial absorbance of sample is calculated by the logarithmic converter 20. Thus, through the subtractor 31, an exact signal freed from fluctuation of light source is memorized in the first memory element in the memory circuit 24. At the same time the absorbance signal memorized in the fourth memory element is supplied to the subtractor 25 as the minuend. Upon advancement of the sample holders, the beams A and B are respectively positioned at a reference side and a sample side, and the switches 30 and 30' are shifted to the contacts $X_b'$ and $X_a'$. Also the switch 23 is shifted to the contact $Y_b$. Thus the absorbance signal of the sample converted by the logarithmic converter 20' is supplied to the subtractor 25 to obtain the difference of absorbance of said sample in one minute, which is further converted to the amount of enzyme by the multiplier 26 and printed by the printer 27.

Figure 7:
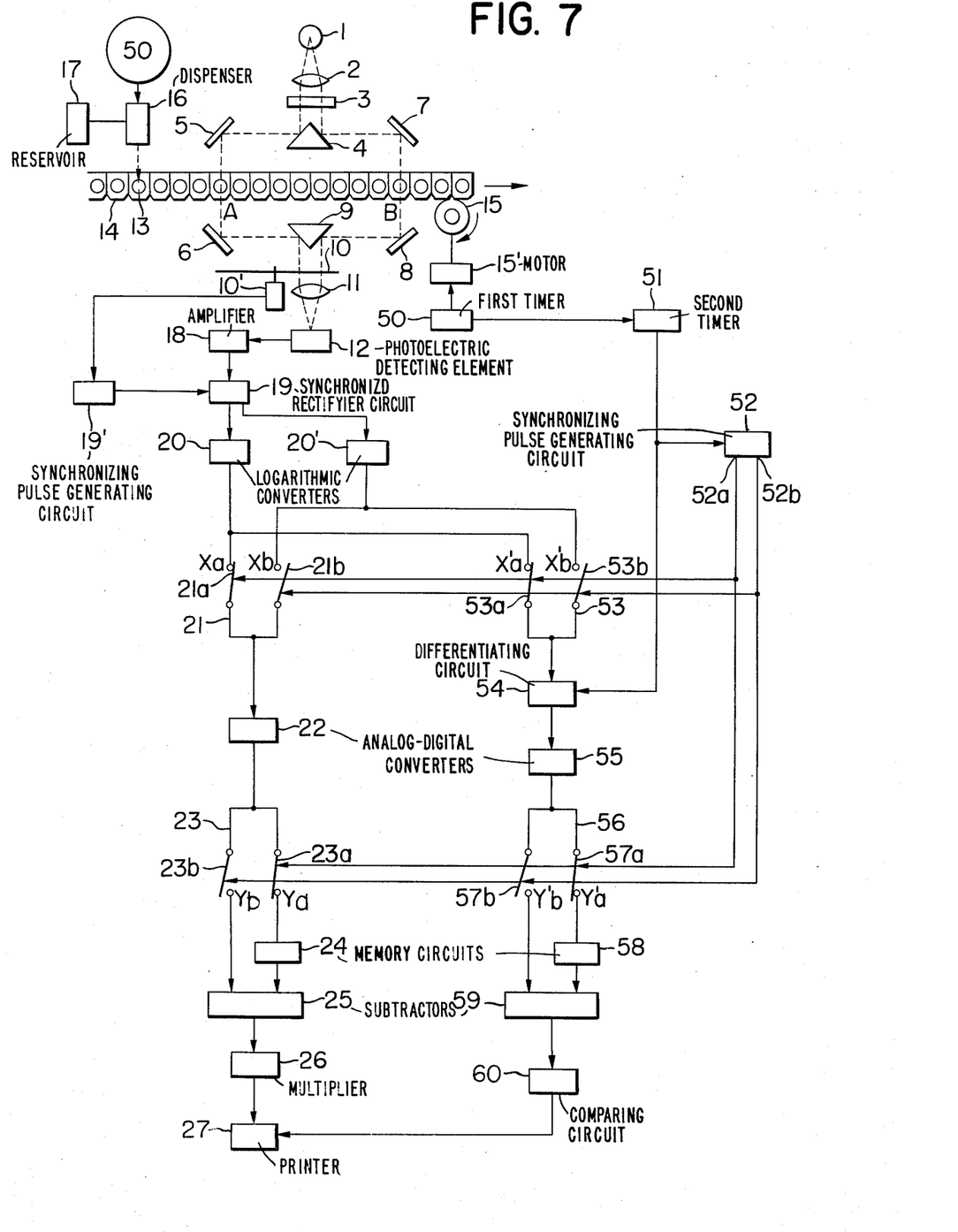
FIG. 7 is a drawing showing a third embodiment of the present invention.

In the following there is given a detailed explanation with particular reference to FIGS. 7 and 8 on a third embodiment for achieving the third object of the present invention. The third embodiment shown in FIG. 7 is composed of the apparatus for measuring the reaction velocity as shown in the first embodiment of the present invention and a differential linearity monitor.

Figure 8A:
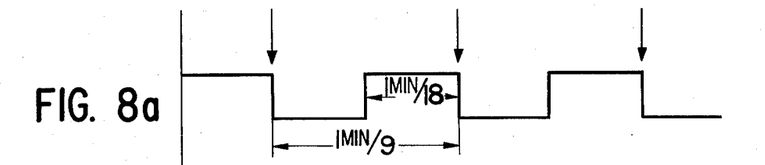
FIGS. 8a – 8d are a pulse chart for explaining the function of principal portion of the third embodiment.
Figure 8B:
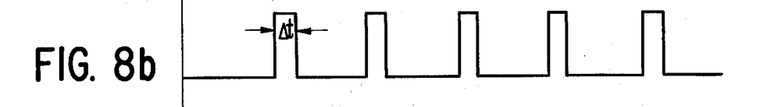
Figure 8C:
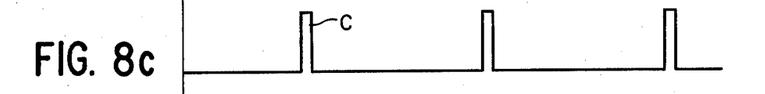
Figure 8D:
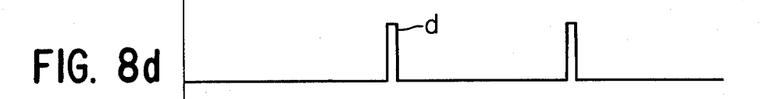

Referring to FIG. 7, 50 is a first timer generating pulses shown in FIG. 8a, for driving the motor 15' which controls the cam 15 so as to advance the cell holders 14 at every 1/9 minute interval. In this manner a cell crossing the beam A reaches the beam B after one minute. The arrow in FIG. 8, indicates the completion of the advance of the sample cells. Further, 51 is a second timer which is put into function for a period $\Delta t$ at the termination or start of the output pulses of the first timer 50 to generate the pulses as shown in FIG. 8b. 52 is a synchronizing pulse generating circuit for generating the pulses $c$ and $d$ as shown in FIG. 8c and FIG. 8d in synchronization with the termination of pulses from the second timer 51, the pulses $c$ and $d$ being alternately released from the output terminals 52a and 52b, respectively. 53 is a switch provided with contacts $X_a'$ and $X_b'$, and switching arms 53a and 53b. 54 is a differentiating circuit for differentiating the absorbance signal from the logarithmic converters 20 or 20' by time upon receipt of output pulses from the second timer 51. Further, 55 is an analog-digital converter, and 56 is a switch provided with contacts Ya' and Yb', and switching arms 57a and 57b. 58 is a memory circuit similar to the aforementioned memory circuit 24 but composed of a ten-unit shift register, of which output is connected to the minuend input terminal of a subtractor 59, of which subtrahend input terminal is connected to the contact Yb'. 60 is a comparing circuit which compares the output of the subtractor 59 with a predetermined tolerance range 0 ± ΔV (ΔV:noise signal etc.) and forwarding the output to the printer 27 when the output is located outside said tolerance range.

The contact Xa, Xa', Ya, or Ya' is closed only when the pulse c shown in FIG. 8C is supplied from the terminal 52a of the pulse generating circuit 52 to the switching arm 21a, 53a, 23a or 57a, respectively. Further the contact Xb, Xb', Yb or Yb' is closed only when the pulse d shown in FIG. 8d is supplied from the terminal 52b of the pulse generating circuit 52.

In the present embodiment of the above-explained composition, the difference between the absorbance at $t_1$ and that at $t_2$ which is one minute later, or the signal indicating the difference of absorbance in one minute is obtained from the subtractor 25, and simultaneously a signal indicating the difference of differentiated absorbances at $t_1$ and $t_2$ is obtained from the subtractor 59. The output signal from the subtractor 25 is multiplied by the K factor in the multiplier 26 to be converted into the amount of enzyme in international units and is printed by the printer 27, while the output signal of the subtractor 59 is compared with aforementioned tolerance range in the comparing circuit 60 and is forwarded to the printer 27 only when said signal is located outside said tolerance range. In this manner, simutaneously with the printing of signal of enzyme amount by the printer 27, the signal from the comparing circuit 60 is printed solely when the output signal 59 is located outside said tolerance range, i.e. when the measurements at $t_1$ and $t_2$ are made in the non-linear portion of reaction, thus enabling to recognize this fact. Such measurements are effected at every interval of 1/9 minute, and the results are printed by the printer 27.

In the following there is given a detailed explanation with reference to FIG. 9 on a fourth embodiment for achieving the second object of the present invention.

Figure 9:
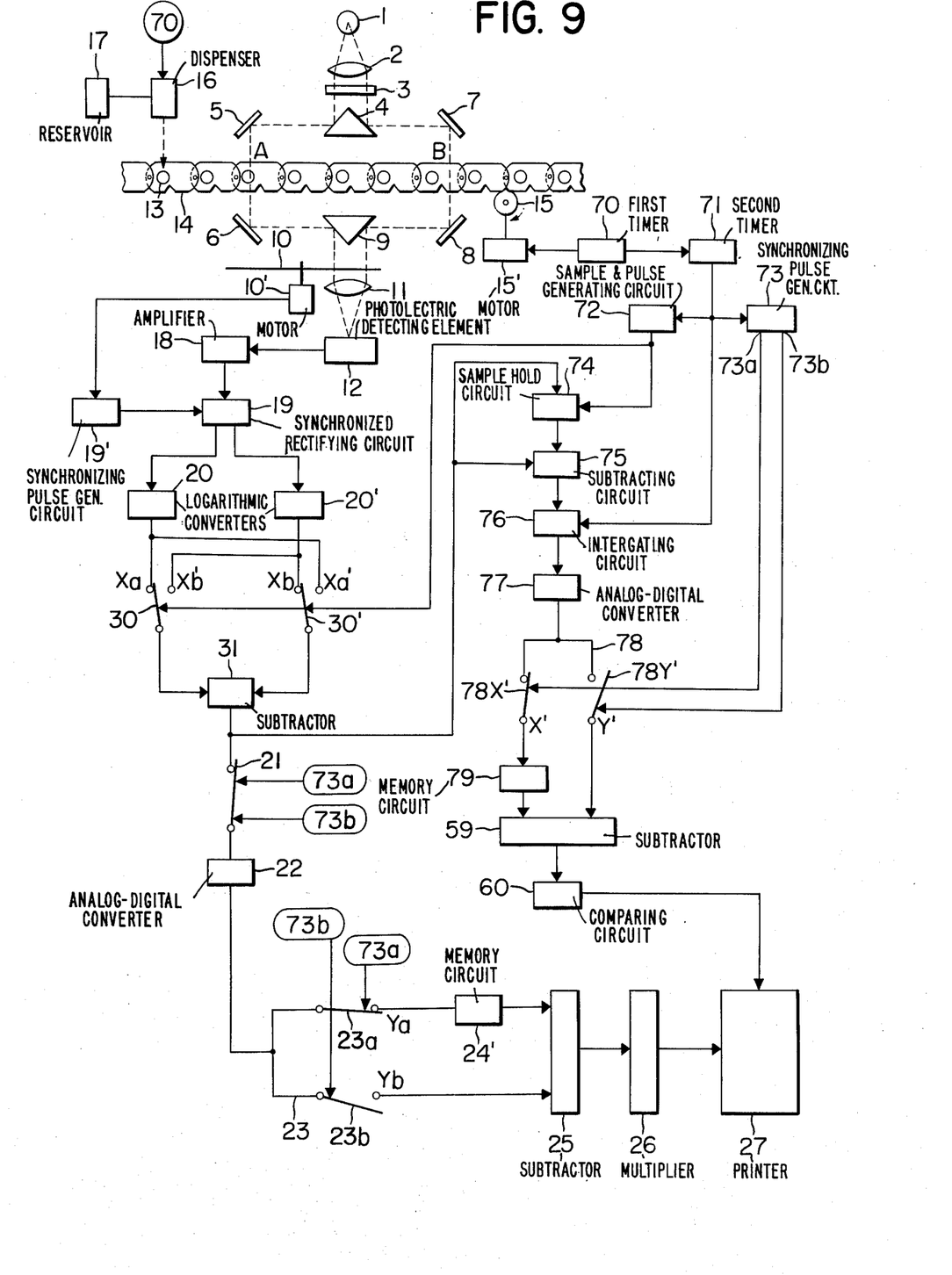
FIG. 9 is a drawing showing a fourth embodiment of the present invention.

The fourth embodiment of the present invention shown in FIG. 9 is composed of an apparatus for measuring reaction velocity of the second embodiment and an integrating linearity monitor.

In this embodiment, simultaneously with the measurement of the absorbance $A_1$ and $A_2$ at $t_1$ and $t_2$, the integrated values of the variation of absorbance at $t_1$ and $t_2$, or the hatched areas in FIG. 11:

$$\int_{t_1-\Delta t}^{t_1} \Delta A_1 dt \text{ and } \int_{t_2-\Delta t}^{t_2} \Delta A_2 \Delta t$$

are measured and mutually compared in order to ebaluate whether the measurements are effected in the linear portion of the reaction.

Figure 10A:
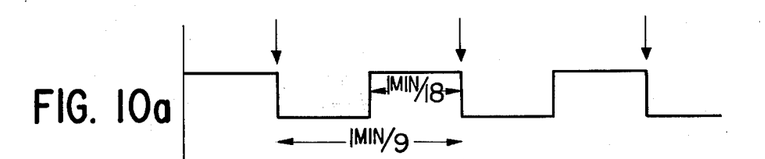
FIGS. 10a – 10d are a pulse chart for explaining the function of principle portion of the fourth embodiment.
Figure 10B:
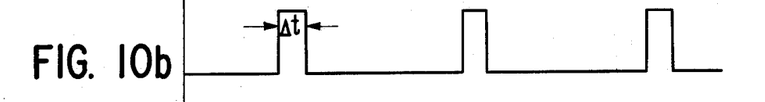
Figure 10C:
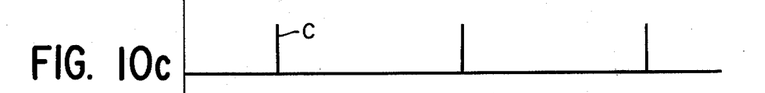
Figure 10D:
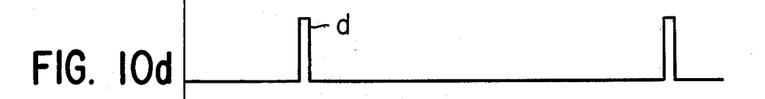
Figure 10E:
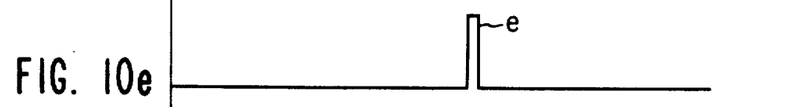

Referring to FIG. 9, 70 is a first timer for generating pulses as shown in FIG. 10d for driving a motor 15', which therefore controls a cam 15 to advance the cell holders 14 at every 1/9 minute interval. Thus the sample cells reach the light beam B one minute after crossing the light beam A. The arrow in FIG. 10a indicates the completion of advancement of sample cells. 71 is a timer similar to aforementioned second timer 51 for generating pulse signals as shown in FIG. 10b. 72 is a sampling pulse generating circuit for generating pulse signals as shown in FIG. 10c at the initiation of each pulse from the timer 71. The switches 30 and 30' are switched over every time those switches receives pulses shown in FIG. 10c from the pulse generating circuit 72. 73 is a synchronizing pulse generating circuit similar to the aforementioned circuit 52 and is provided with terminal 73a and 73b for generating respectively the pulses d and e shown in FIGS. 10d and 10e. Switches 23 and 78 are controlled in such a manner that the switching arms 23a and 78'x thereof come in contact with the contancts Ya and X' upon receipt of the pulse d and the switching arms 23b and 78'Y come into contact with the contancts Yb and Y' thereof upon receipt of the pulse e. The switch 21 is closed only when it receives the pulses d and c. 74 is a sample hold circuit which is put into function for a determined period at least equal to Δt, upon receipt of the pulse c from the sampling pulse generating circuit 72, to hold the absorbance signal from the subtracting circuit 31 for said period and supply said signal to a subtracting circuit 75, which receives, as the minuend, the absorbance signal from the subtracting circuit 31 to obtain the difference of said two input signals. 76 is an integrating circuit which is put into function upon receipt of the pulse shown in FIG. 10b from the timer 71 to integrate the absorbance signal from the subtracting circuit 75. 79 is a memory circuit similar to the circuit 24 and composed of a five-unit shift register.

In the present embodiment of the composition explained above, the subtractor 59 generates a signal indicating the difference between the integration of the absorbance signal from $t_1 - \Delta t$ to $t_1$ and that from $t_2 - \Delta t$ to $t_2$ wherein $t_2$ is one minute after $t_1$. Said difference signal is compared in the comparing circuit 60 with aforementioned tolerance range and forwarded to the printer 27 only if said difference signal is located outside said tolerance range. In this manner, simultaneous with the printing of the signal indicating the amount of enzyme by the printer 27, the signal from said comparing circuit 60 is also printed if the measurements at $t_1$ and $t_2$ are made in a non-linear portion of the reaction thereby enabling to recognize this fact. Such measurements are effected at every 1/9 minute interval, and the results are printed by the printer 27.

Although the foregoing explanation has been concentrated on the measurement of velocity of enzymatic reaction, the apparatus of the present invention is generally applicable effectively for the analysis of the phenomena wherein the absorbance of a given wavelength of reaction product, and particulary of the zero-order reactions. For example the redox reaction of thytochrome C can be measured by the detection of absorbance at 510 nm. Furthermore, it is naturally easily possible to design electric circuit for calculating the reaction velocity of first-order reactions from the absorbances at time $t_1$ and $t_2$.

I claim:

1. Apparatus for measuring the velocity of a chemical reaction by detecting changes in light absorbance proportional to time comprising: means for maintaining a plurality of samples at regular spaced intervals, means intermittently advancing said samples at constant intervals relatively to first and second exposure stations, detection means including colorimetric sample exposure means and a detector for detecting the light absorbance of said samples upon exposure, said exposure means including means simultaneously exposing the samples at said first and second stations, means transmitting absorbance signals alternately from the exposed samples to said detector, and means for determining the reaction velocity of each sample from the difference of light absorbance measurements thereof detected at the times of exposure of each sample at said two different stations, said apparatus further including reflecting means arranged to direct absorbance light signals from said stations to said detector and means provided between said reflecting means and said detector alternately to permit said absorbance signals from said first and second stations to reach said detector.

2. Apparatus for measuring the velocity of a chemical reaction by detecting the changes in light absorbance of samples in which said reaction is taking place, said apparatus comprising:

means for generating a light beam and for dividing said beam into separate light beams and directing each separate light beam along separate light beam paths, means for moving said samples relatively to said light beam paths so that each sample crosses each light beam path and becomes exposed to a separate light beam at first and second times, respectively, with a given number of other samples becoming exposed to the first separate beam once between said first and second times, a light absorbance detection device, means directing the separate beams alternately to said detection device after said respective separate beams expose a sample, said detection device producing a signal corresponding to the light absorbance of each sample thus exposed, a signal memory device connected to receive signals from said detection device produced by exposure of each sample by one of said separate beams, said memory device being capable of storing said given number of signals in sequence and for successively reading out the earliest applied signal as each new signal is applied thereto from said detection device, and a signal subtraction device connected to receive signals from said detection device produced by exposure of each sample by the other of said separated beams and from said memory device and to produce a difference signal corresponding to the difference in light absorbance of each sample at said first and second times respectively.

3. Apparatus according to claim 2, including means operative to identify a non-linear condition of said reaction velocity at said first and second times.

4. Apparatus according to claim 3, wherein said means operative to identify said non-linear condition include a circuit operative in response to said light absorbance measurements taken at said first and second times to produce control signals corresponding to the rates of change of light absorbance of said reaction velocity at each of said first and second times, a subtractor for obtaining the difference of said two control signals, and means operative to produce an abnormality signal in response to the output of said subtractor when such output exceeds a predetermined standard level.

5. Apparatus according to claim 4, wherein said circuit to produce control signals is a differentiating circuit.

6. Apparatus according to claim 4, wherein said circuit to produce control signals is an integrating circuit.

7. A method for measuring the velocity of a chemical reaction by detecting changes in light absorbance proportional to time comprising:

generating a light beam, dividing said light beam into separate beams, directing each separate beam along separate light beam paths, moving said samples relatively to said light beam paths so that each becomes exposed to a separate light beam at first and second times, respectively, with a given number of other samples becoming exposed to the first separate beam once between said first and second times, producing a signal corresponding to the light absorbance of each sample thus exposed, storing said given number of signals in sequence and successively reading out the earliest applied signal as each new signal is produced, and producing a difference signal corresponding to the difference in light absorbance of each sample at said first and second times, respectively.

8. Apparatus for measuring the velocity of a chemical reaction by detecting the changes in light absorbance of samples in which said reaction takes place, said apparatus comprising:

a. means for generating a light beam and for dividing said beam into first and second light beams and directing each such divided light beam along corresponding first and second light beam paths;

b. means for holding said samples in a line;

c. means for intermittently moving the holding means in one direction to successive resting states along said line so that when each sample moves from one resting state to another a new sample becomes positioned in the first light beam and a second sample, previously exposed to the first light beam, becomes positioned in the second light beam path, and so that each sample becomes positioned for exposure to the first and second light beams at a predetermined time interval;

d. a light absorbance detection device;

e. means directing the first and second light beams alternately to said detection device while the samples are being exposed to said light beams so that said detection device produces signals corresponding to the light absorbance of each sample thus exposed;

f. a signal memory device connected to receive signals from said detection device produced by exposure of each sample to the first light beam, said memory device being capable of storing in sequence a number of signals corresponding to the number of resting states between said first and second light beam paths and for successively reading out the earliest signal as each new signal is applied thereto from said detection device; and g. a signal subtraction device connected to receive signals from said detection device produced by exposure of each sample to the second light beam and from said memory device and to produce a difference signal corresponding to the difference in light absorbance of each sample at said time interval.

9. Apparatus according to claim 8, further comprising means operative to identify a non-linear condition of said reaction velocity at said time interval.

10. Apparatus for measuring the velocity of a chemical reaction be detecting the changes in light absorbance of samples in which said reaction takes place, said apparatus comprising:
   a. light generating means for generating a light beam and for dividing said beam into first and second light beams and for directing each such light beam along corresponding first and second light beam paths;
   b. holding means for holding said samples in a line so that each sample is spaced from next adjacent samples by a predetermined distance to define space portions of said holding means;
   c. moving means for intermittently moving the holding means in one direction to successive resting states along said line, said holding means and moving means being arranged in conjunction with said light generating means to produce alternately, at successive resting states, a first condition in which a new sample is exposed to said first light beam and simultaneously therewith a space portion of the holding means, between two previously exposed samples, is exposed to said second light beam and a second condition in which a previously unexposed space portion of the holding means between samples is exposed to said first light beam and simultaneously therewith a sample previously exposed to said first light beam is exposed to said second light beam, each sample being exposed to the first and the second light beams at a predetermined time interval;
   d. a light absorbance detection device;
   e. means arranged to direct each of said first and second light beams alternately to said detection device during the time each sample remains in a resting state so that said detection device produces, alternately, a sample signal corresponding to the light absorbance of a sample and a reference signal corresponding to the light absorbance of a space portion;
   f. a first signal subtraction device connected with said detection device to produce a differential signal between the sample signal and the corresponding reference signal produced at each resting state of said moving means;
   g. a signal memory device connected to the first signal subtraction device to memorize first differential signals which are produced during each said first condition, said memory device being capable of storing, in sequence, a number of the first differential signals corresponding to the number of resting states between said first and second resting states and for successively reading out the earliest applied first differential signal as each new first differential signal is applied thereto; and
   h. a second subtraction device connected to the first subtraction device to receive second differential signals which are produced during each second condition and further connected to receive the signals read out from said memory device to produce a third differential signal between each first differential signal read out from the signal memory device and the corresponding differential signal then being produced, said third differential signals corresponding to the change in light absorbance of the samples at said time interval.

11. Apparatus according to claim 10, further comprising means to identify a non-linear condition of said reaction velocity at said time interval.

12. A method for measuring the velocity of a chemical reaction by detecting the changes in light absorbance of samples in which said reaction is taking place, said method comprising:
   a. generating a light beam;
   b. dividing said light beam into first and second light beams;
   c. directing each light beam along a separate light beam path;
   d. holding said samples in a line;
   e. moving said samples intermittently, but in unison, in one direction to successive resting states along said line so that at each resting state a new sample is positioned in the first light beam path and, simultaneously therewith, a sample previously exposed to the first light beam is positioned in said second light beam path so that sample becomes positioned for exposure to the first and second light beams at a predetermined time interval;
   f. producing, at each resting state, a first signal corresponding to the light absorbance of the sample exposed to the first light beam and a second signal corresponding to the light absorbance of the sample exposed to the second light beam;
   g. storing, in sequence, a number of said first signals corresponding to the number of resting states between said light beam paths and successively reading out the earliest applied first signal as each new first signal is produced; and
   h. producing a difference signal corresponding to the difference between the first signal read out from storage and the second signal then produced.

13. The method according to claim 12, further comprising the step of determining a linear condition of said reaction velocity at said time interval.

14. A method for measuring the velocity of a chemical reaction by detecting the changes in light absorbance of samples in which said reaction is taking place, said method comprising:
   a. generating a light beam;
   b. dividing said light beam into first and second light beams;
   c. directing each light beam along a separate light beam path;
   d. holding said samples in a line so that each sample is spaced from next adjacent samples by a predetermined distance to define space portions;
   e. moving said samples intermittently, but in unison, in one direction to successive resting states along said line to produce, alternately, at successive resting states, a first condition in which a first sample is exposed to said first light beam and simultaneously therewith a first space portion between two previously exposed samples is exposed to said second light beam and a second condition in which a previously unexposed second space portion between two samples is exposed to said first light beam and simultaneously therewith a second sample, previously exposed to said first light beam, is exposed to said second light beam, each sample being moved from said first light beam to said second light beam at a predetermined time interval, f. producing a first differential signal between a signal corresponding to the light absorbance of said first sample and a first reference signal corresponding to the light absorbance of said first space portion at each resting state in said first condition;

g. producing a second differential signal between a signal corresponding to the light absorbance of said second sample and a second reference signal corresponding to the light absorbance of said second space portion at each resting space in said second condition;

h. storing, in sequence, a number of the first differential signals corresponding to the number of resting states between said first and second resting states and successively reading out the earliest of stored signal as each new signal is stored; and i. producing a differential signal between the first differential signal read out from storage and the second differential signal then produced.

15. The method according to claim 14, further comprising the step of determining a non-linear condition of said reaction velocity at said time interval.

16. Apparatus for measuring the velocity of a chemical reaction by detecting the changes in light absorbance of samples in which the reaction is taking place, said apparatus comprising:

a. holding means for holding said samples in a line;

b. moving means for intermittently moving the holding means in one direction along said line so that each sample comes to rest, for a predetermined length of time, at each of several successive resting places along said line;

c. light absorbance detection means arranged to produce, within each said predetermined length of time, first and second electrical signals corresponding, respectively, to the light absorbance of the samples which are present at first and second ones of said resting places, respectively, during such predetermined length of time, d. a signal memory device connected to receive said first signals from said detection means, said memory device being capable of storing in sequence a number of said first signals corresponding to the number of resting places between said first and second resting places and for successively reading out the earliest received first signal as each new first signal is received from said detection means; and e. a signal subtraction device connected to receive, during each said predetermined length of time, each second signal from said detection device and each first signal then being read out from said memory device to produce a difference signal corresponding to the difference in light absorbance of each sample over the time interval during which said sample moves from said first to said second resting place.

17. A method for measuring the velocity of a chemical reaction by detecting the changes in light absorbance of samples in which the reaction is taking place, said method comprising the steps of:

a. holding said samples in a line;

b. intermittently moving said samples in unison in one direction along said line so that each sample comes to rest for a predetermined length of time at each of several successive resting places along said line;

c. producing, within each said predetermined length of time, first and second electrical signals corresponding, respectively, to the light absorbance of the samples which are present at said first and second ones of said resting places, respectively, during such predetermined length of time;

d. storing a number of said first signals in sequence, said number corresponding to the number of resting places between said first and second ones of said resting places, and successively reading out the earliest stored first signal as each new first signal is produced; and e. producing a difference signal corresponding to the difference between each first signal being read out from storage during production of each second signal to produce a difference signal corresponding to the difference in light absorbance of each sample over the time interval during which said sample moves from said first to said second resting place.

* * * * *

UNITED STATES PATENT AND TRADEMARK OFFICE
CERTIFICATE OF CORRECTION

PATENT NO. : 4,063,817
DATED : December 20, 1977
INVENTOR(S) : TERUO SHIMAMURA, et al.

It is certified that error appears in the above-identified patent and that said Letters Patent are hereby corrected as shown below:

Column 1, line 59, change the "÷" to -- + --; line 60, change "is" to -- in --.
Column 3, line 28, change "10d" to -- 10e --; line 50, change "semi-circuit" to -- semi-circular --.
Column 4, line 10, change "is" to -- in --.
Column 6, line 15, change "24" to -- 24' --; line 21, change "24" to -- 24' --; line 33, change "24" to -- 24' --; line 58, delete the second "the".
Column 7, line 62, change "ebalu-" to -- evalu- --.
Column 11, line 8, change "reaction be" to -- reaction by --.

Sheet 5 of the drawings should appear as shown on the attached sheet.

Signed and Sealed this

Twentieth Day of June 1978

[SEAL]

Attest:

RUTH C. MASON
Attesting Officer

DONALD W. BANNER
Commissioner of Patents and Trademarks